United States Patent
Lam et al.

(10) Patent No.: US 7,405,056 B2
(45) Date of Patent: Jul. 29, 2008

(54) TISSUE PUNCH AND TISSUE SAMPLE LABELING METHODS AND DEVICES FOR MICROARRAY PREPARATION, ARCHIVING AND DOCUMENTATION

(76) Inventors: Edward Lam, 3260 Keller St., Santa Clara, CA (US) 95054; Ronald Lam, 112 Crooked Creek Trail, Barrington, IL (US) 60010

( * ) Notice: Subject to any disclaimer, the term of this patent is extended or adjusted under 35 U.S.C. 154(b) by 55 days.

(21) Appl. No.: 11/071,598

(22) Filed: Mar. 2, 2005

(65) Prior Publication Data

US 2006/0199169 A1 Sep. 7, 2006

(51) Int. Cl.
*G01N 33/48* (2006.01)
*A61B 10/00* (2006.01)

(52) U.S. Cl. .................. 435/40.5; 435/40.52; 600/562; 600/564

(58) Field of Classification Search ........................ None
See application file for complete search history.

(56) References Cited

U.S. PATENT DOCUMENTS

| | | | |
|---|---|---|---|
| 5,002,377 | A | 3/1991 | Battifora et al. |
| 6,103,518 | A | 8/2000 | Leighton |
| 6,383,801 | B1 | 5/2002 | Leighton |
| 6,406,840 | B1 | 6/2002 | Li et al. |
| 6,466,690 | B2 | 10/2002 | Bacus et al. |
| 6,468,783 | B1 | 10/2002 | Leighton |
| 2002/0009767 | A1 | 1/2002 | Muraca |
| 2002/0106626 | A1 | 8/2002 | Muraca |
| 2002/0127631 | A1 | 9/2002 | Schiller et al. |
| 2002/0132246 | A1 | 9/2002 | Kallioniemi et al. |
| 2002/0146813 | A1 | 10/2002 | Leighton |
| 2002/0168639 | A1 | 11/2002 | Muraca |
| 2002/0192702 | A1 | 12/2002 | Konenen et al. |
| 2002/0197656 | A1 | 12/2002 | Li et al. |
| 2003/0017446 | A1 | 1/2003 | Chasse et al. |
| 2003/0215936 | A1 * | 11/2003 | Kallioniemi et al. ..... 435/287.1 |

FOREIGN PATENT DOCUMENTS

| | | |
|---|---|---|
| WO | WO 99/44062 | 9/1999 |
| WO | WO 99/44063 | 9/1999 |
| WO | WO 00/24940 | 5/2000 |
| WO | WO 00/51812 | 9/2000 |
| WO | WO 00/52132 | 9/2000 |
| WO | WO 01/22086 | 3/2001 |
| WO | WO 01/42796 | 6/2001 |
| WO | WO 01/98525 | 12/2001 |
| WO | WO 02/48680 | 6/2002 |
| WO | WO 02/065118 | 8/2002 |

OTHER PUBLICATIONS

Wan et al. A Rapid and Effcient Method for Testing Immunohistochemical Reactivity Agains Multiple Tissue Samples Simultaneously; Journal of Immunological Methods, vol. 103, No. 1 (1987) pp. 121-129.*

* cited by examiner

*Primary Examiner*—Jon P Weber
*Assistant Examiner*—Paul C. Martin
(74) *Attorney, Agent, or Firm*—Townsend & Townsend & Crew LLP; Mark D. Barrish

(57) ABSTRACT

A workstation that provides an efficient method to collect biological tissues in a column tissue array format from blocks of embedded, frozen tissues, or fresh tissues. The workstation has a control unit for directing operations of the workstation and the operation unit for performing the production of the tissue column array. The operation unit comprises an array of vertical tubes in a platform, an arbor which engages and presses down the designated tube in the array, the embedded tissue block which is mounted directly below the designated tube, assemblies of motors responsive to the control unit for driving the platform and the tissue block, a light source block for generating an alignment signal, and a light detector block which measures the signal from the light source to determine the degree of alignment between the arbor, punch tubes, and the specimen block.

24 Claims, 13 Drawing Sheets

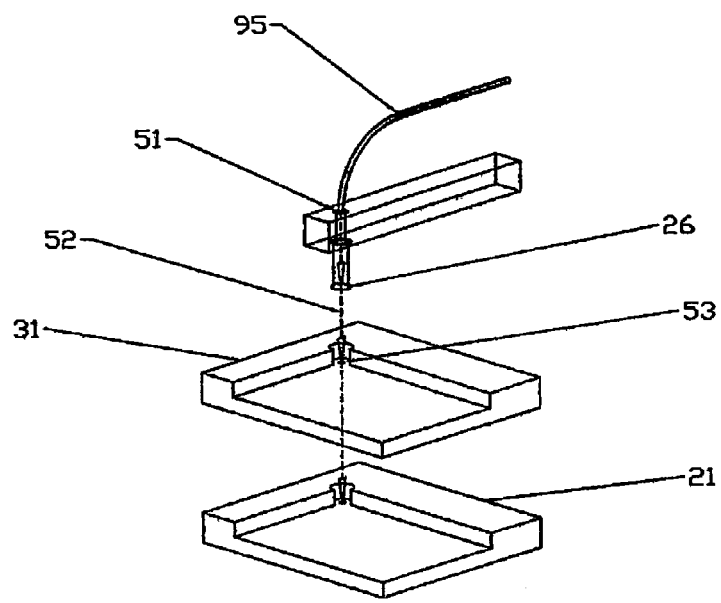
FIG. 7A
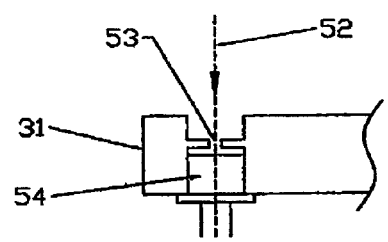
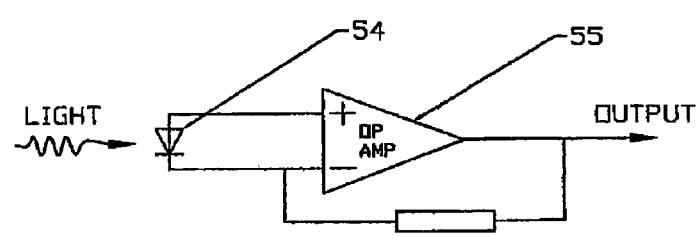
FIG. 7B      FIG. 7C

TISSUE PUNCH AND TISSUE SAMPLE LABELING METHODS AND DEVICES FOR MICROARRAY PREPARATION, ARCHIVING AND DOCUMENTATION

CROSS-REFERENCES TO RELATED APPLICATIONS

Not Applicable

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

This invention generally relates to tissue handling and preparation of tissue for biological analysis, and in particular embodiments provides methods, devices, and systems using labeled punch tubes in the preparation of tissue microarrays and microarray slides, for tissue sample archiving, for correlating pathology, histology, and other biological test results with specific source tissues through intermediary tissue configurations, and the like.

Punch tubes are often used to obtain samples of tissue specimens for biological testing. The tissue specimens are often removed surgically from patients, and punch tubes can help to separate a desired sample of the tissue which is appropriate for the planned test from the remaining tissue specimen. In many cases, a thin section or slice of a tissue sample from the punch tube is placed on a glass slide or other test substrate.

Glass slides are widely used in biological analysis of punch tissues, and the use of biological analysis of tissue slides is likely to grow tremendously in the future. The expanding range of analytical techniques that can be applied to tissue slides and the increasing use of these techniques for studying, diagnosing, and monitoring disease states may challenge the current capacity of laboratories to accurately prepare tissue slides, to reliably handle large numbers of test tissues, and to document the sources of these test tissues.

To increase the throughput of tissue analysis techniques and decrease the resources dedicated to each analytical test, slides are being prepared with a number of individual test tissues on each slide. Typically, several tissue punch samples are embedded in a paraffin block, and the block is sectioned into thin slices. The individual slices are placed onto glass slides, and the slides are then subjected to microscopic examination or other testing procedures. For example, the slides can be used for diagnosis based on cell morphology and staining characteristics of the samples. Further, it is possible to evaluate multi-sample slides with histological approaches such as in situ hybridization for genetic studies, immunochemistry for antigen (e.g. protein) studies, and the like. A large (and growing) number of alternative techniques have been and are now being developed to test tissues on glass slides and other substrates.

By placing more samples on each slide, it is often possible to analyze more tissues in parallel. Such multi-tissue slides are also amenable to high throughput analysis, and it is possible to study collections of normal and/or diseased tissues in a single experiment. Practical applications of multi-sample slides range from diagnostics to drug target validation to a host of other uses. Through the use of precision instrumentation, it has become possible to construct multi-sample slides containing large numbers of samples in defined locations. These slides are sometimes called tissue microarrays, and have been prepared using a number of different techniques.

While known tissue microarray preparation techniques have achieved varying levels of success in allowing labs to handle tissues for testing, the currently available methods may generally suffer from deficiencies that have limited their use. For example, many involve time consuming, labor intensive, and highly repetitious processing steps that can introduce errors and inaccuracies. At least some of these methods could lead to cross contamination between samples, and/or degradation of tissues between specimen removal and the biological tissue testing. Some or all of these methods may lack adequate flexibility and security for selectively handling tissues from a variety of sources and preparing them for any of a number of different tests, some of which tests (for example) need not be performed until long after the associated specimens have been removed from the patient and results from initial tests on tissue samples from the specimen have been obtained.

In light of the above, it would be desirable to have improved methods, devices, and systems for the efficient handling of tissues for biological testing, preparation of tissue microarrays and other tissue test-related articles, and test tissue tracking.

BRIEF SUMMARY OF THE INVENTION

The present invention generally provides improved methods, devices, and systems for handling and preparation of tissues for biological analysis. In many embodiments, the improved techniques provided by the present invention make use of an array or set of punch tubes, with the punch tubes often being supported by a punch tube platform which allows each tube to slide along its axis. The punch tubes can extend from the platform into a tissue specimen that has been removed from a patient so as to capture a tissue sample within a receptacle of the punch tube. The punch tubes and/or platform may have a label (such as a barcode or radiofrequency identification device ("RFID")) indicating one or more tube or sample identifiers. By labeling the specimen removed from the patient, the punch tubes, a microarray block containing a plurality of the samples, and each microarray slide separated from the microarray block, and by recording the relationships therebetween, a continuous tissue identification chain can be established between a test result at a specific location of a microarray slide and a tissue sample location within a tissue specimen of a particular patient. Such a tissue identification chain can help avoid errors when testing large numbers of biological tissues from different tissue specimens and different patients. Exemplary techniques for punching tissue samples from tissue specimens while recording the tissue sample locations are also provided, and the punch tubes (with their associated tissue samples) may be archived and/or reassembled into new tissue arrays by selectively removing punch tubes from one platform and/or selectively assembling punch tubes into another platform. In some embodiments, cooling of the punch tubes, tissue specimen, and/or tissue samples can be provided using cryogenic and/or other cooling techniques, and microarray blocks may be prepared efficiently and with little waste of tissue or time by aligning the tissue samples from the punch tubes both axially and laterally within the microarray block using the punch tube platform.

In a first aspect, the invention provides a method for preparing a microarray from a tissue specimen. The method comprises extending a plurality of punch tubes from a punch tube platform so that a distal end of each punch tube advances into the tissue specimen. An associated tissue sample protrudes from the specimen into a sample receptacle of the punch tube, and the punch tubes and their associated tissue samples are removed from the tissue specimen.

Optionally, a plurality of other platforms may be provided, with each platform having openings for receiving punch tubes. A platform identifier associated with each platform may be recorded, and each platform may have a platform label indicating the associated platform identifier. The platform label may comprise a barcode, an RFID tag, or the like.

In many embodiments, at least some of the tissue specimens will be extruded from the punch tubes to form a tissue microarray. Typically, at least four punch tubes are extended by sliding the tubes from the platform, and the punch tubes may slide serially and/or sequentially. The platform can hold the punch tubes in a two-dimensional punch tube array so that the punch tubes slide along parallel longitudinal axes. The sample receptacle of each punch tube may punch the associated sample with a sample cross section suitable for use in a tissue microarray, with the tube receptacle typically having a cross sectional dimension of between about 0.4 mm and 0.5 mm. Conveniently, the platform may support each punch tube with a separation distance from an adjacent punch tube that is also appropriate for the tissue microarrays, with the sample separation distance between adjacent tissue samples typically being in a range of up to about 5.0 mm (measured between tissue sample centers). This can facilitate extruding the tissue samples from the array of punch tubes into the microarray while the punch tubes are supported by the platform. The platform will often support between about 1 and about 1,000 punch tubes.

Optionally, at least some of the tissue samples may be extruded by a plunger array having a plurality of plungers. The plungers of the plunger array may correspond to some or all of the punch tubes supported by the platform, and the plungers may have aligned distal plunger surfaces so that the samples are extruded with their proximal surfaces aligned. The samples may be extruded toward a mold, and an embedding agent may be added to the mold and allowed to cure so as to form a tissue sample microarray block. A plurality of tissue sample microarray blocks may be formed using other tissue samples and a microarray block identifier may be recorded for each microarray block. Each microarray block may have a microarray block label indicating the associated microarray block identifier. The labels may comprise a barcode, an RFID tag, or the like.

The microarray blocks may be separated into a plurality of microarray sections. A microarray section identifier for each microarray section may be recorded, and each microarray section may be labeled with a microarray section label indicating the associated identifier. The microarray section label may comprise a barcode, an RFID device, or the like, and an association between the microarray section identifier and the tissue samples, tissue specimen, and an associated patient may also be recorded. These and other recordation steps described herein will often comprise storing the identifiers and associations in a tangible media using machine-readable code. In many embodiments, the tissue samples, the tissue specimen, and/or the platform may be cryogenically cooled.

An identifier associated with each punch tube will often be recorded. In many embodiments, each punch tube identifier will be associated with a tissue specimen identifier and a patient identifier. The punch tube may have a punch tube label indicating the punch tube identifier and the punch tube label may comprise a barcode, an RFID device, or the like. In some embodiments, at least some of the punch tubes may be removed from the platform while the removed punch tubes contain the associated tissue samples. At least one of these removed punch tubes may be mounted on another platform. The other platform can receive a different plurality of punch tubes. The punch tubes may have different associated tissue samples, so that more than one tissue sample may be associated with the array of punch tubes on a platform.

Optionally, at least one of the tissue samples may be archived within the associated punch tube for use significantly after removal of the at least one tissue sample from the tissue specimen. Advantageously, the punch tube label may be used to identify the tissue sample contained by the punch tube.

The punch tubes will often be extended distally into the tissue specimen by an arbor. Each punch tube may be urged proximally from the tissue specimen using a spring, with the arbor resiliently deforming the spring during extension. In other embodiments, the arbor may both extend and retract the punch tubes. The arbor may simultaneously advance at least two of the punch tubes in to the tissue specimen. The arbor may sequentially advance a second punch tube after a first punch tube, and the tissue specimen may be repositioned relative to the arbor using a first motion stage between use of the first and second punch tubes. In an exemplary embodiment, the platform is repositioned relative to the arbor by a second motion stage between use of the first and second punch tube.

The motion stages may be zeroed by transmitting light from an illumination source to at least one light sensor. The illumination source may be at a fixed reference location during motion of the motion stages. A first registration aperture may be adjacent a platform receptacle for zeroing the second motion stage, while a second registration aperture adjacent a specimen receptacle is used for zeroing the first motion stage. Zeroing may be effected by maximizing the light through one or both of these apertures.

After using the first punch tube to capture the first tissue sample, a second tissue sample may be manually input to an input device with reference to a slide tissue. The slide tissue may correspond to and be separated from the tissue specimen. The first motion stage may move the slide tissue and tissue specimen while maintaining registration therebetween. A system operator may view a display showing an image of the slide tissue, along with a target marker identifying a candidate location for a subsequent tissue sample. The target marker may be projected onto the slide tissue, or may be superimposed on the image using image processing techniques or the like. The first motion stage may effect lateral movement of the target marker to an alternative candidate location by moving the slide tissue laterally relative to a field of view of an image capture device coupled to the display. The arbor can remain aligned with the image capture device during movement of the first motion stage. In some embodiments, a plurality of prior punch tube sample locations may be displayed on the slide tissue image. This can help the user to select appropriate tissue samples, as the slide the user is viewing may, unlike the tissue specimen itself, may undergo no physical change so as to indicate where samples have already been removed.

In another aspect, the invention provides a system for preparing a microarray from a tissue specimen. The system comprises a plurality of punch tubes, each punch tube having a proximal end, a distal end, and a sample receptacle disposed near the distal end for receiving an associated tissue sample when the distal end of the tube is advanced into the tissue specimen. A punch tube platform may have a plurality of openings, with each opening slidably receiving a punch tube therein.

The platform will often slidably receive at least four punch tubes. The punch tubes may be held in a two-dimensional array, with the punch tubes slidable along parallel axes. The samples may be intended for tissue microarray analysis that defines a tissue sample cross sectional size range and a tissue sample separation range. The sample receptacle of each punch tube may have a cross section in the size range, and each opening may be separated from adjacent openings by a separation in the separation range.

Each punch tube may have a chamfer disposed radially outwardly about the sample receptacle so as to form a sharpened distal edge at the distal end of the punch tube. A cross section of the punch tube receptacle and/or sample may remain substantially constant proximal the sharpened edge. This can facilitate proximal entry of the tissue sample into and distal extrusion of the sample from the sample receptacle. In some embodiments, a friction-inhibiting coating may be disposed along an outer surface of the punch tube and/or an inner surface of the punch tube.

A machine readable punch tube identifier may be associated with each punch tube. The punch tube identifier may have a recorded association with a tissue specimen identifier and a patient identifier. Each punch tube identifier may be indicated by a label disposed on the associated punch tube. The label may comprise a bar code, an RFID device, or the like. A platform identifier may be associated with the platform, and a platform label may be disposed on the platform to indicate the platform identifier, often using a machine readable format. A tangible media record may indicate an association between the platform, the punch tubes mounted thereon, one or more tissue specimens, and one or more patients.

Biasing means may couple each punch tube to the platform so as to withdraw the punch tube and tissue sample proximally from the tissue specimen. In some embodiments, punch tubes may have a coupling for releasable engagement by an associated coupling of the arbor to facilitate withdrawing the punch tubes proximally using the arbor. Each punch tube may have a proximal stop extending radially beyond the associated opening of the punch tube platform. The proximal stop may engage the platform adjacent the opening so as to limit distal travel of the punch tube. The biasing means may comprise a compression spring extending between the proximal stop and the platform.

In many embodiments, a punch tube arbor may drive the distal ends of the tubes distally into the tissue specimen. The tissue samples may remain disposed within the openings when the punch tubes are withdrawn proximally. In some embodiments, the arbor may be configured to simultaneously advance at least two punch tubes into the tissue specimen. The arbor may be configured to sequentially advance a second punch tube after a first punch tube. Optionally, a tissue specimen receptacle may hold the tissue specimen, and a first motion stage may couple the tissue specimen receptacle to the platform. A controller coupled to the first motion stage may be configured to align the second punch tube with a second location of the tissue specimen after the first punch tube captures a first tissue sample from a first location of the tissue specimen. A second motion stage may couple the arbor to the platform, and the controller may be configured to align the arbor with the second punch tube after the first punch tube captures the first tissue sample.

An illumination source may transmit zeroing light toward one or both of the motion stages. A first registration aperture may be disposed adjacent to the platform, and a second registration aperture may be disposed adjacent the specimen receptacle. At least one light sensor may zero the first motion stage and the second motion stage by maximizing the zeroing light through the first registration aperture and through the second registration aperture.

An input may be coupled to the controller for manually inputting the second location. A slide receptacle may receive the slide having slide tissue corresponding to (and separated from) the tissue specimen. The slide receptacle may be coupled to the specimen receptacle so as to maintain registration therebetween. An image capture device having a field of view encompassing some or all of the slide tissue may be coupled to a display adjacent the input, allowing the display to show an image of the slide tissue. A target marker can identify a candidate location for a subsequent tissue sample, with the target marker optionally being projected onto the slide tissue, superimposed on the display image, or the like.

The first motion stage may effect lateral movement of the target marker to an alternative candidate location by moving the slide receptacle laterally relative to the field of view of the image capture device. As the specimen receptacle moves in registration with the slide receptacle, the arbor can remain aligned with the image capture device at a fixed location.

For extrusion of the samples from the punch tubes, a plunger array may have a plunger base supporting a plurality of plungers. The plungers of the plunger array may correspond to at least some of the punch tubes supported by the platform, and may have aligned distal surfaces. This can allow the plungers to be advanced distally into the punch tubes so that they extrude a plurality of the tissue samples with proximal tissue surfaces of the samples aligned.

In another aspect, the invention provides a method of preparing a biological sample microarray block. The method comprises capturing a set of biological sample portions within a set of receptacles. One or more of the samples are extruded from the receptacles toward a mold. An imbedding agent is added to the mold, the agent contacting the sample portions. The agent is allowed to cure, thereby forming the biological sample microarray block.

Two or more of the sample portions may be captured serially, and two or more of the sample portions may be captured simultaneously. The set of sample portions may be captured from a plurality of biological samples. The sample portions may be serially excluded from the receptacles and/or at least some of the sample portions may be simultaneously extruded from the receptacles. The sample portions may be captured from one or more tissue specimens by advancing the receptacles therein, the receptacles comprising punch tubes. The sample portions may be extruded so as to engage an adhesive lining of the mold.

In another aspect, the invention provides a device for preparing a biological sample microarray block. The device comprises an arbor that engages a set of receptacles and urges the set of receptacles to contact a biological specimen and capture a set of sample portions therefrom. A plunger can engage the set of receptacles to extrude one or more of the sample portions toward a mold. At least one processor module may be coupled to the arbor and the plunger so as to control the movement thereof.

Optionally, a memory may store a location corresponding to the positions on the tissue specimen from which the tissue sample portions have been taken. The memory may store an associated receptacle identifier corresponding to each sample location.

In another aspect, the invention provides a tissue punch microarray system for identifying specimens from a plurality of patients. The system comprises a plurality of tissue specimens including a first specimen and a second specimen. A plurality of tissue specimen identifiers help identify tissue samples taken from the first and second specimens. A first microarray block identifier helps identify a first microarray block. The first microarray comprises a first group of the samples. A second microarray block identifier identifies a second microarray block comprising a second group of the samples. A plurality of microarray slides are separated from the first microarray block, each having a microarray slide label indicating a microarray slide identifier. A tangible media stores each microarray slide identifier. The tangible media indicates, for each microarray slide: a microarray block identifier of an associated microarray block from which the microarray slide was separated; the tissue sample identifiers of associated tissue samples included in the associated microarray block; at least one tissue specimen identifier of an associated tissue specimen from which the associated tissue samples were taken; and at least one patient identifier of the patient from which the associated specimen was taken.

In the exemplary embodiment, a plurality of punch tubes are provided for separating the tissue samples from the associated tissue specimen and for containing the tissue samples therein. Each punch tube has a machine readable punch tube label indicating the sample identifier of the sample therein. A plurality of punch tubes may be supported by a punch tube platform so as to allow each punch tube to separate the associated tissue sample from the associated tissue specimen and contain the tissue sample therein. The platform may have a machine readable platform label.

In yet another aspect, the invention provides a tissue punch microarray system for identifying specimens from a plurality of patients. The system comprises a plurality of tissue samples. A plurality of punch tubes each contain an associated tissue sample and have a machine readable punch tube label. Tangible media stores, for each sample, an associated punch tube identifier of the punch tube label and a patient identifier of the patient associated with the sample.

BRIEF DESCRIPTION OF THE DRAWINGS

FIGS. 7A-7C schematically illustrate structures and methods for optical alignment or zeroing of motion stages supporting the punch tube platform, a specimen receptacle, and a press arbor of the workstation of FIG. 1.

DETAILED DESCRIPTION OF THE INVENTION

The present invention generally provides improved devices, systems, and methods for handling of tissues for biological analysis. Exemplary embodiments of the invention provide improved devices, systems, and methods for preparing microarray blocks and slides from tissue samples taken from one or more tissue specimens. Punch tubes will often be used to separate the tissue samples from the tissue specimens, and each punch tube will often include a label indicating a punch tube identifier that can be used to identify a tissue sample contained within a receptacle of the punch tube. The labels may comprise bar codes, radiofrequency identification ("RFID") devices, or the like, and similar labels may be placed on the tissue specimen block, a microarray block formed from the samples, the microarray slides taken from a microarray block, and the like. The punch tubes may be releasably mounted to a platform that allows the punch tubes to slide for collection of the samples, and the platform may also have a label. By storing the identifiers indicated by the labels, the systems, devices, and methods described herein may allow a continuous chain of data to associate a microarray slide (or even a specific tissue location within the array of a microarray slide) to a patient (or even a specific specimen block location of a specimen taken from the patient). By recording and documenting the relationships between the patient ID and the discreet test tissues, inadvertent testing errors, retesting, inaccurate test results, and testing resource waste can be significantly reduced.

In one embodiment of the present invention, fabrication of tissue microarray blocks can be separated into two tasks, which may be performed sequentially or simultaneously. One task is the collection of tissues or samples in an array format. Another task is the embedding of tissues in array format.

Figure 1:
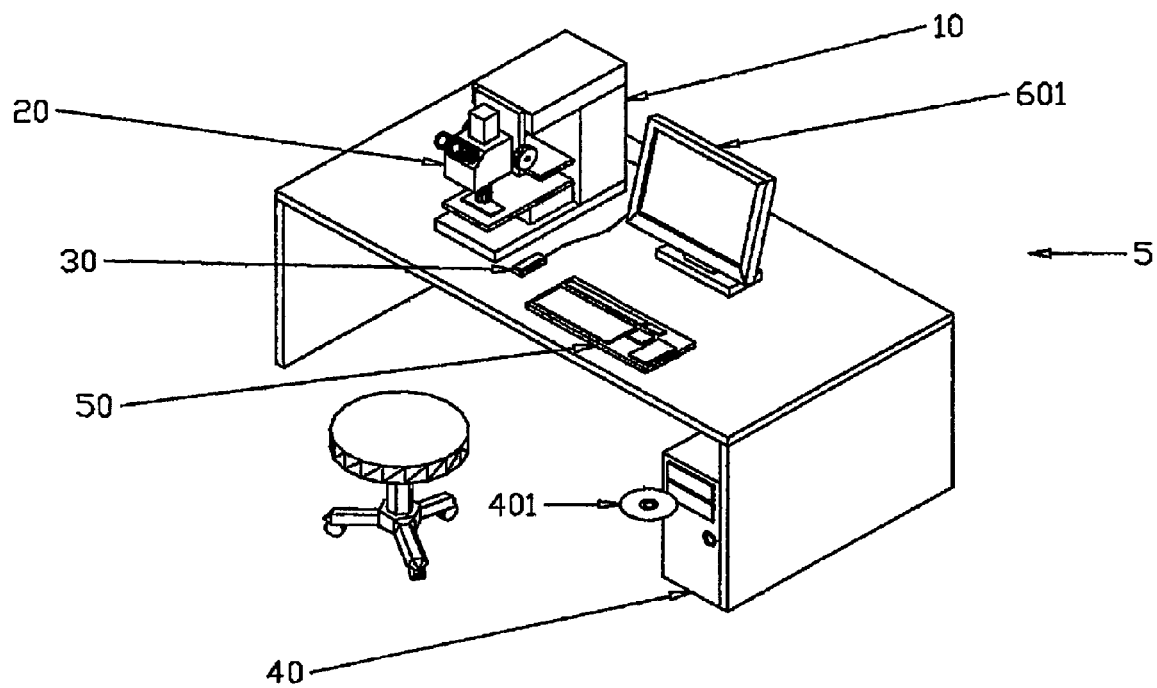
FIG. 1 illustrates a perspective view of a workstation in accordance with one embodiment of the present invention.

FIG. 1 shows an automated workstation 5 in accordance with one embodiment of the present invention. Workstation 5, in front of which an operator may be seated, can include an operation unit 10 and a control unit 40. Operation unit 10 can perform collection steps to manufacture a column tissue array (CTA) under the direction of control unit 40. Each column of the column tissue array may comprise a tissue sample obtained from a tissue specimen using a punch tube. Operation unit 10 can also perform embedding steps to manufacture a sample microarray block from the CTA. Communication between the operator and control unit 40 can be effected through a graphic display 601, a keyboard 50, and a hand operated switch 30. For example, switch 30 can be used to control a punching process, as further described below. Operation unit 10 can be directed using control unit 40, so that a large variety of CTA's may be prepared. A microscope and CCD camera assembly 20 coupled with operation unit 10 can be used to survey and identify an area of interest on a tissue slide.

Figure 2:
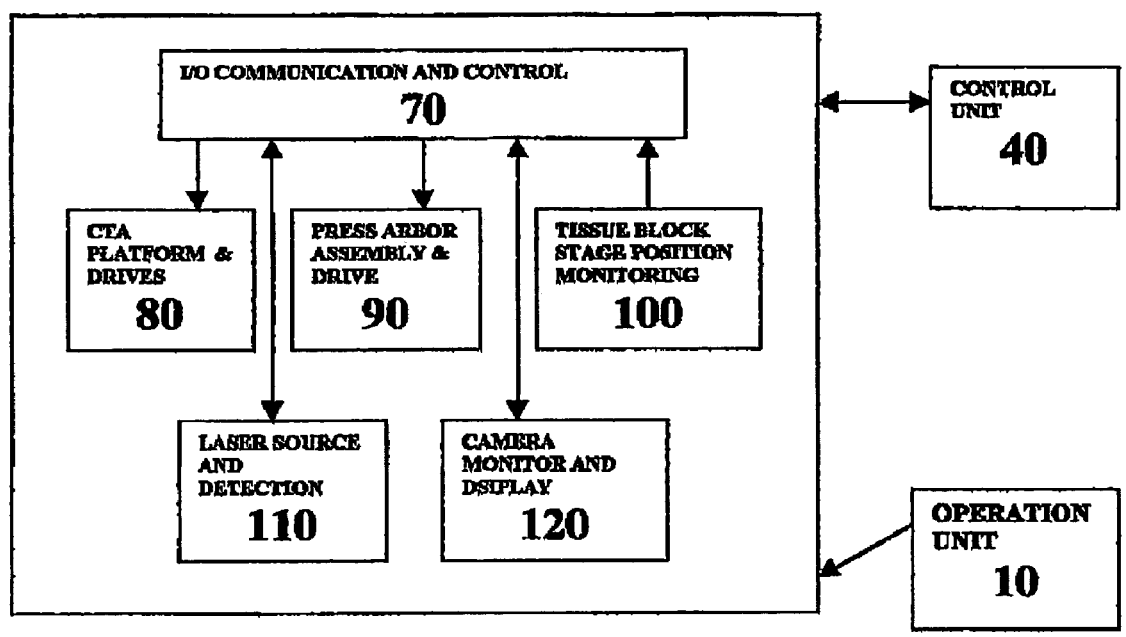
FIG. 2 provides a block diagram illustrating components and a general organization of the workstation of FIG. 1, the components broadly including a control unit and an operation unit.

FIG. 2 presents a general organization of operation unit 10 and control unit 40 according to one embodiment of the present invention. Control unit 40, which may comprise a personal computer, typically communicates with operation unit 10. Operation unit 10 can include an input/output communication and control system 70, a press arbor system 90, a CTA stage system 80, a tissue block and sample slide stage system 100, a light source and detection system 110, and a CCD camera and graphic display system 120. Operation unit 10 can also include a plunger system.

Referring to both FIGS. 1 and 2, control unit 40 generally includes a processor which is used as a controller for effecting the methods described herein, often under the direction of the system operator. Controller 40 will often include hardware, software, firmware, or the like used for implementing some or all of these method steps described herein, and in many embodiments will include a tangible media 401 embodying a machine readable programming code with instructions for implementing these method steps and/or associated data. The tangible media 401 may include an optical disk or other optical media storage, a magnetic disk or tape or other magnetic recording media, a random access memory, a read only memory, a memory stick device, or the like. In some embodiments, the instruction steps and/or data may be transmitted to control unit 40 using any of a wide variety of transmission modalities including the Internet, an Intranet, an Ethranet, a local or wide area network, a wireless connection, optical signals, or the like.

While the exemplary embodiment is illustrated with control unit 40 having a single personal computer tower, some or all of the data processing may be performed by boards mounted to or near one or more components of the operation unit 10, or the processing may be distributed between localized boards of the operation unit, one or more personal computers, or the like, in a wide variety of distributed or centralized data processing architectures. Similarly, the machine readable code may comprise a single program, or may be written as a plurality of programs or subroutines in any of a variety of different code architectures. In some embodiments, aspects or portions of control unit 40 may be referred to as modules, with the modules typically comprising hardware and/or software for implementing some portion (or all) of the associated methods.

Figure 3:
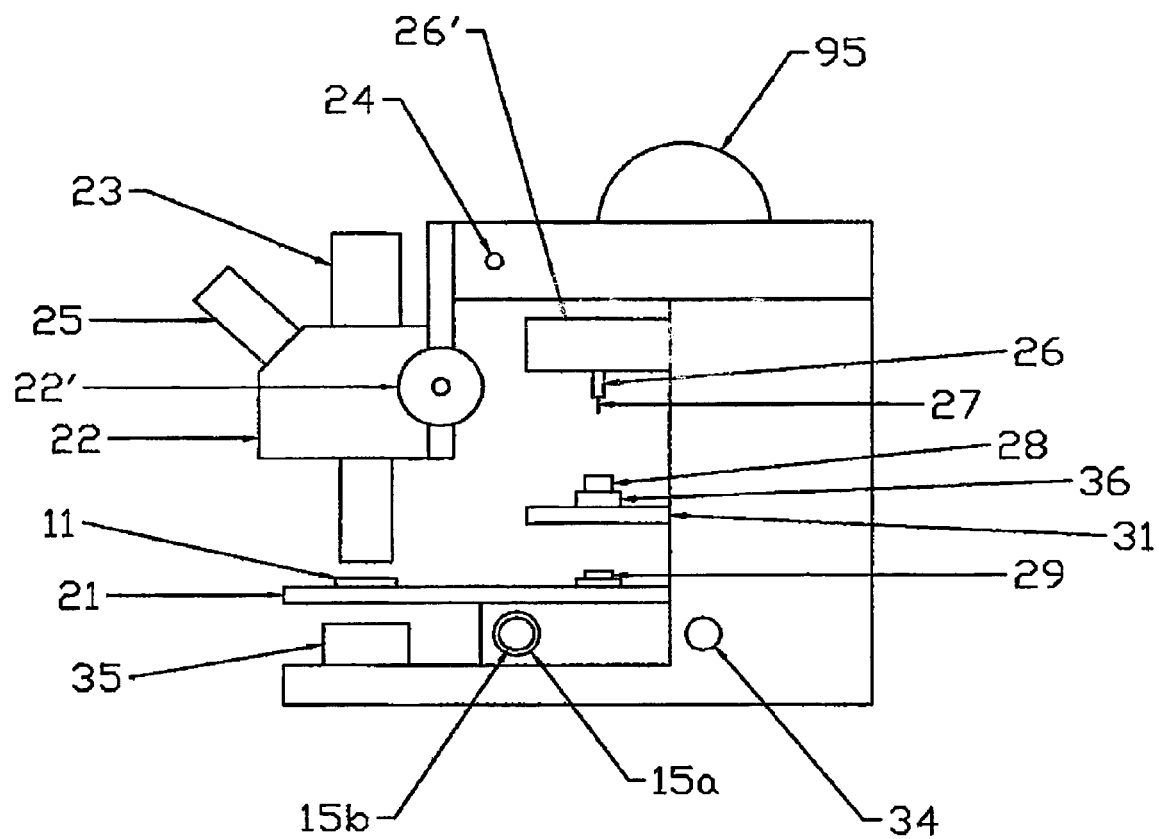
FIG. 3 illustrates a side view of an operation unit of the workstation of FIG. 1.

FIG. 3 shows a detailed view of operation unit 10 according to one embodiment of the present invention. Microscope and CCD camera assembly 20 typically include a microscope 22, a CCD camera 23, an eyepiece 25, and a knob 26, and can be swung upward and downward about a hinge 24, according to the needs of the operator. For example, microscope and CCD camera assembly 20 can be swung upward and out of the way of the operator. A tissue slide 11 and a tissue specimen block 29 can be placed on or otherwise coupled with a tissue block motion stage 21. A knob 34 can be turned to raise or lower tissue block stage 21, for example in order to position the tissue block just below a CTA motion stage 31. A CTA or punch tube platform 36 can contain or be coupled with a set of receptacles such as an array of punch tubes 28, and can be mounted onto CTA stage 31. Control unit 40 (see FIG. 1) can direct CTA stage 31 to a location where a designated punch tube is directly below a press arbor 27. Press arbor 27 can be mounted to a chuck 26 that is attached to a press arbor platform 26'. CTA stage 31 and tissue block stage 21 working zeroes can be individually calibrated by a collimated light beam transmitted through arbor 27 via a fiber optic cable 95.

Microscope 22 and CCD camera 23 can be focused onto tissue slide 11 by adjusting knob 22'. A condenser 35 can be located below sample tissue slide 11. An image of the sample tissue slide 11 can be observed through eyepiece 25 or via graphic display 60, which can be a flat panel display. The operator may survey horizontally different locations on sample tissue slide 11 for an appropriate or desired area by adjusting the two knobs 15a and 15b. Because tissue slide 11 and tissue block 29 are typically aligned on the tissue block stage 21, and usually conform to the same coordinate system, the respective positions on slide 11 and on block 29 will typically be congruent to each other. Thus, a candidate tissue sample on tissue slide 11 can be determined by an image of a cross hair in eyepiece 25. The corresponding position on tissue block 29 will often be located at the center of a designated punch tube (aligned below press arbor 27). Once the desired location on tissue specimen slide 11 is found, the operator may activate handheld switch 30 to activate operation unit 10 to collect a sample from tissue block 29.

FIG. 4A shows certain aspects of operation unit 10 which can be directly involved in the manufacturing of a sample receptacle array, according to one embodiment of the present invention. Array of punch tubes 28 can be supported on CTA or punch tube platform 36 which is mounted on or coupled with CTA stage 31. CTA stage 31 is capable of two directional independent translational lateral motions (in the x and y horizontal directions). In this way, any desired designated tube 28a of punch tube array 28 can be shifted horizontally into position directly under press arbor 27. Tissue block motion stage 21 is capable of movement in two or three translational degrees of freedom, including horizontal x and y motion. Alternative embodiments of operation unit 10 are also possible.

Figure 5:
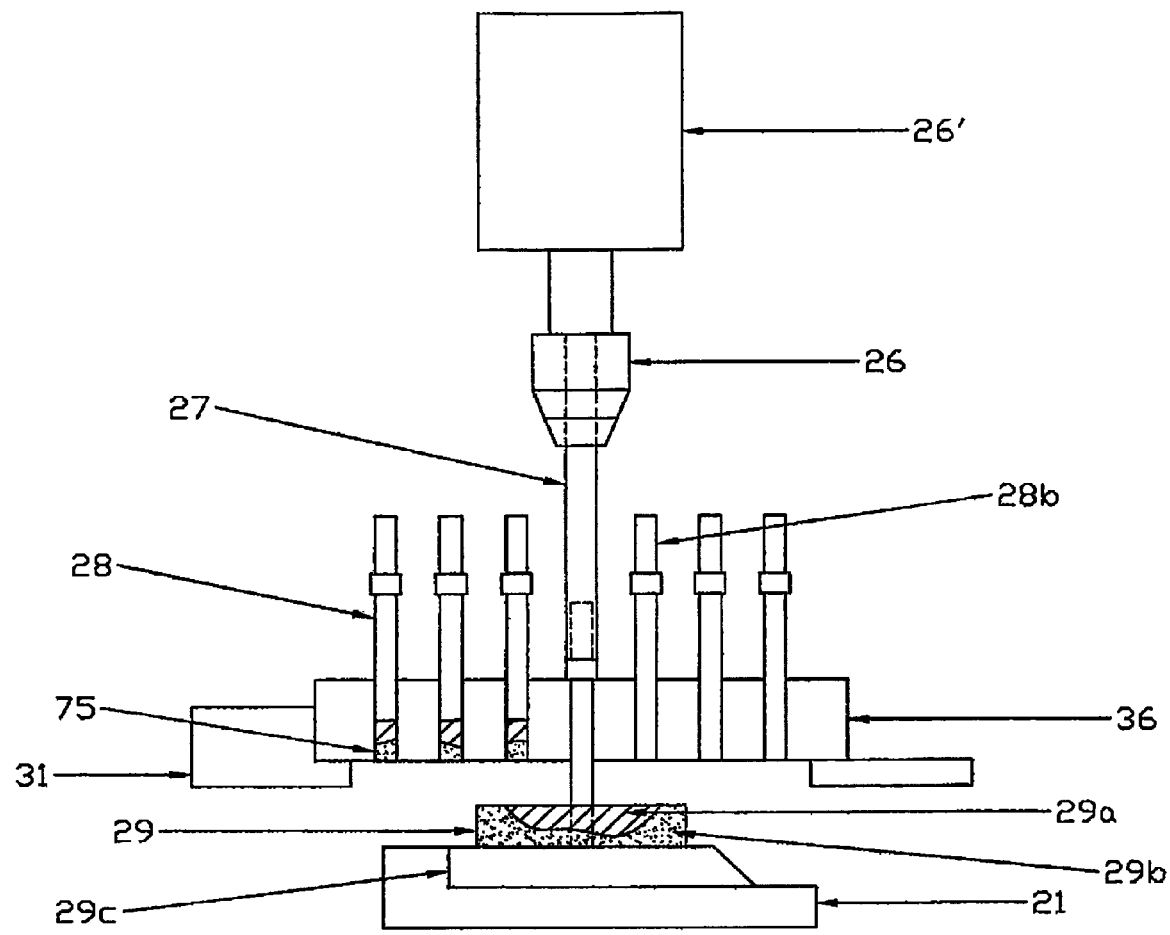
FIG. 5 is a side view schematically illustrating the punching action of the tissue sample from the tissue specimen block during use of the workstation of FIG. 1.

As shown in FIG. 5, press arbor stage 26' an move press arbor 27 vertically to engage designated punch tube 28a on CTA platform 36. Designated punch tube 28a thus can make an excursion downward and penetrate tissue block 29. On retraction of designated punch tube 28a from tissue specimen block 29, a sample can be collected in tube 28a. CTA platform 36 can then be moved by the CTA motion stage 31 to align with another designated punch tube 28b within array 28, and the collection process can be repeated. As shown in this figure, donor specimen block 29 can include a tissue sample 29a and embedding agent 29b, along with a positioning cassette 29c.

Donor specimen block 29 can be prepared in a variety of ways. In one approach, a specimen 29a can be placed toward the bottom of a block die. The die can be loaded with an embedding agent 29b. A first cassette 29c can be placed on top of the loaded die. When agent 29b has cured, the cassette 29c, agent 29b, and embedded specimen can be separated from the die, and inverted as shown in FIG. 5. Specimen 29a, which was originally toward the bottom of the die, is now toward the top of specimen block 29. The top side of specimen block 29 can be sectioned or microtomed until a satisfactory portion of specimen 29a is exposed. The height of the sectioned specimen block 29 may vary. The sectioned specimen block 29 can optionally be placed in a second die and the second die can be loaded with additional embedding agent to obtain a predetermined thickness using a second cassette 172. An opening in the second cassette may allow a core sample to be taken from the top side of the specimen block as well as from the bottom side of block 29. It is also possible to further process a donor specimen block by melting or removing the embedding medium 29b of the block, re-embedding the specimen 29a in a cassette with partial or no grid/slotted support, and filling the cassettes with embedding medium to a predetermined height or thickness. The block may then be sampled from either the top side or the bottom side.

Figure 6:
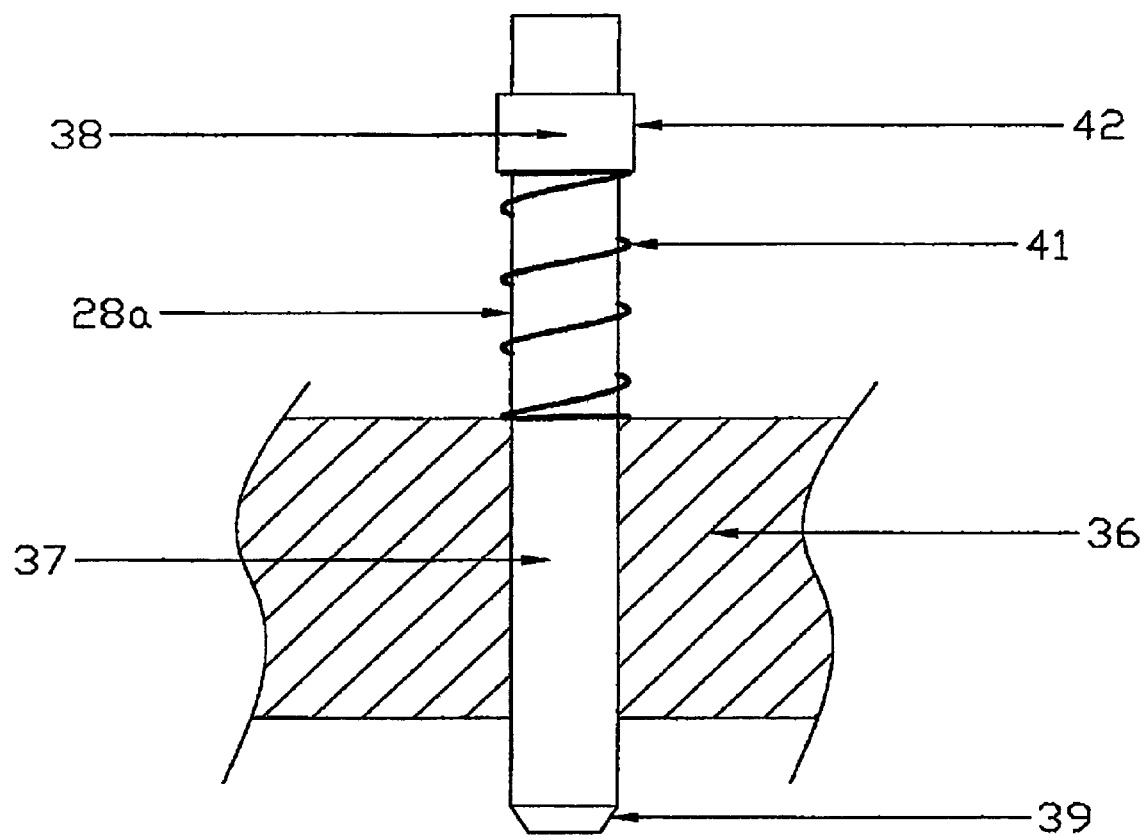
FIG. 6 is a partial cross-sectional side view illustrating the structure of and sliding engagement between a punch tube having an RFID band and an associated platform, for use in the workstation of FIG. 1.

FIG. 6 illustrates a cut-away view of punch tube of CTA platform 36 according to one embodiment of the present invention. Each punch tube 28a of the array 28 can be made of hardened material such as stainless steel and beryllium copper (for low temperature usage), and can have a wall of varying widths. For example, the wall of tube 37 can be as thin as about 0.005". A distal edge 39 of tube 37 may be chamfered for easy cutting of the core sample. Tube 37 can be biased relative to CTA platform 36 by a spring 41 that aids in retracting punch tube 37 from tissue block 29 (not shown in this figure). The inside and/or outside surfaces of tube 37 may be electropolished to a mirror finish, and coated with a very thin layer of titanium oxide to reduce friction during the insertion and retraction process so that distortions in the adjacent sample or cells may be minimized or prevented. A stop collar 38 can define the maximum excursion. Label 42, which can be separate from, part of, and/or in cooperative association with stop collar 38, can emit modulated radio frequency digital ID signals upon request. This way, each punch tube 28a can be independently identified and archived, optionally as the associated sample is taken. CTA platform 36 can support the array of punch tubes 28. For low temperature operations, CTA platform 36 can be made of or include high thermal conductive materials such as copper. The temperature can be maintained by attaching a micro-refrigerator such as a Peltier cooling device.

As can be understood with reference to FIGS. 5 and 6, press arbor 27 will be positioned directly above a selected punch tube 28a. Retraction of punch tube 28a can be accomplished by a variety of means, such as a compression spring, as shown in FIG. 6, or the press arbor itself while returning to its initial position. From the retracted position, punch tube 28a can be extended by press arbor 27, which urges punch tube 28a toward donor specimen block 29 to collect a sample portion 75. For example, press arbor 27 can optionally have a pin that engages an "L-shaped" slot of punch tube to allow rotation and retraction of the arbor to move the engaged punch tube proximally. Punch tube 28a is usually in a retracted position in platform 36. In the case of a compression spring, the spring can compress as punch tube 28a is extended distally, and can decompress as punch tube 28a is retracted. In some cases, one or more punch tubes can be slotted along at least a portion of their length to provide an elongated window, allowing for observation of the contents therein. For example, it may be possible to view the length and location of sample 75.

Three dimensional motion of press arbor 27, as well as any of the other components of operation unit 10, can be accomplished by any of a variety of means, including by pneumatics or by one or more electric motor, which can be in turn controlled by a computer or microprocessor of control unit 40. In this way, it is possible, for example, to carefully direct the speed and the distance of the press arbor movements. Likewise, the motion of tissue block stage 31 can be accomplished by similar means. In fact, any component of operation unit 10, such as stage 31, can optionally be movable in three dimensions to a desired position, and such movement can be effected by any combination of mechanical, electrical, and computer-based modules. Movement of press arbor 27 and array platform 36 can be useful for aligning the punch tubes 28a with the samples. Relatedly, the x-y motion of platform 36 can be controlled by a computer such that the receptacle coordinates, array, and sample identities are stored. For example, for an N×M array of punch tubes, the receptacle punching sequence can be chosen from (1,1) to (1,N); (2,N) to (2,1); and so on until the last receptacle (N,M) contains a sample.

FIGS. 7A-7C show detailed views of the alignment of press arbor 27 to CTA stage 31 and tissue block stage 21 respectively, according to one embodiment of the present invention. Light beam 52 can be generated by a light source such as a laser and delivered to press arbor chuck 26 via optical fiber 95. A collimating lens can convert a divergent beam from the end of fiber 95 into a pencil parallel beam of light 52. CTA stage 31 can have a small aperture 53 located at a corner of two perpendicular resting surfaces where CTA platform 36 (not shown here) sits. As shown in the embodiment illustrated in FIG. 7B, a small photo detector diode 54 can be situated behind or otherwise underneath aperture 53. CTA stage 31 can be moved to a position so that aperture 53 is intercepting optimally the beam 52 coming from above. The exposure of light 52 to the photodiode 54 can cause current to flow across the device. In the embodiment shown in FIG. 7C, a current signal can be converted into a voltage signal by a operational amplifier 55. A device such as a voltmeter can monitor this signal voltage. At the position of maximum voltage output, CTA stage 31 will typically be aligned to the press arbor chuck 26 and arbor 27. By moving CTA stage 31 out of the way, one can direct light beam 53 to align tissue block stage 21 in a similar procedure.

In some embodiments, laser beam 53 can be used to identify a selected location on specimen 29a of donor block 29. Laser beam 53 can travel through a central aperture of press arbor 27, through a central aperture of punch tube 28a, and onto a surface of donor block 29. The location where laser beam 53 hits block 29 can be visualized directly by the operator. In this way, the operator can move the donor block 29 until an area of interest is located directly beneath receptacle 28a.

Donor block 29 can optionally be processed to include alignment features such as fiduciary marks. For example, two or three fiducial holes can be drilled into block 29. The location of the holes will often be situated at the corner or edge of specimen 29a. Fiducial marks such as these can establish and/or confirm a Cartesian coordinate reference on the specimen. Often, biological studies or tests will involve the preparation of multiple donor specimen blocks, which may be from one or more patients.

Figure 4:
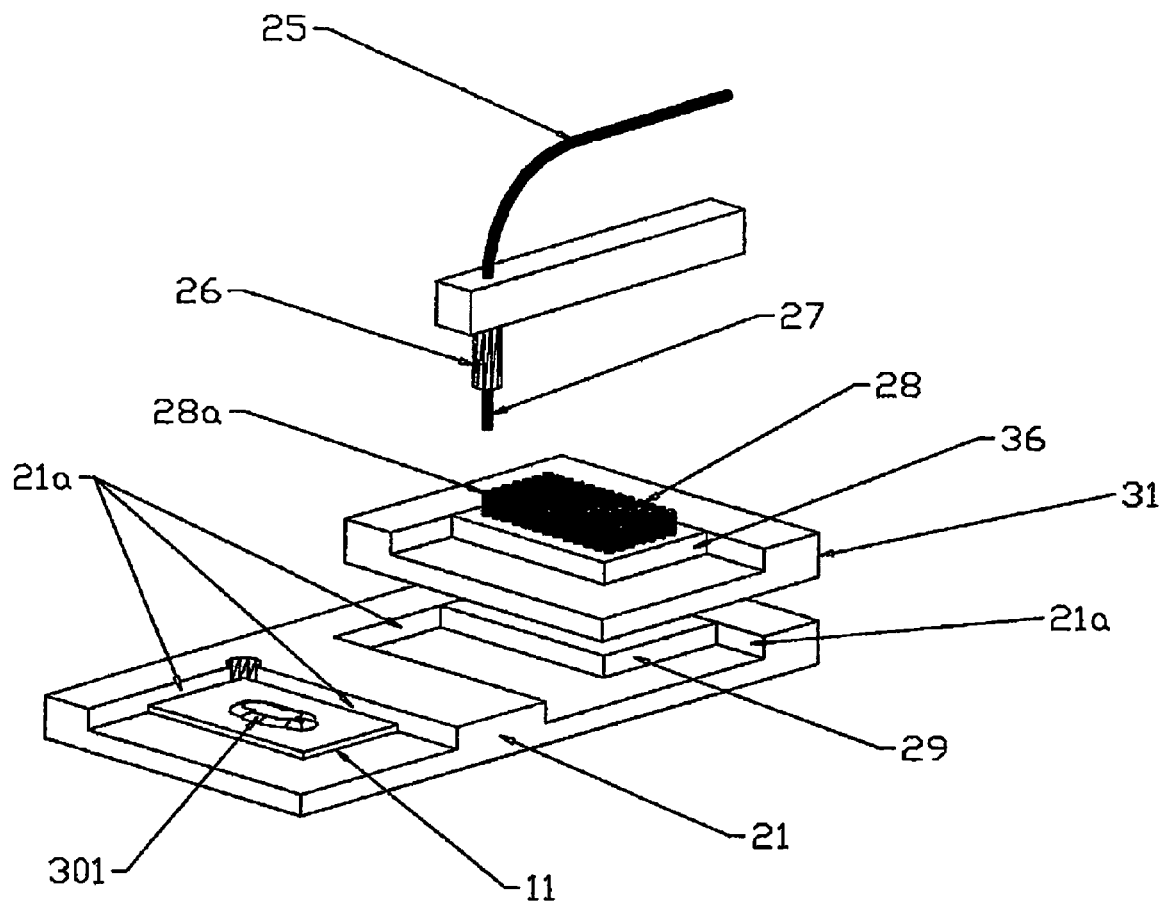
FIG. 4 illustrates a perspective view of a punch tube tissue array platform, arbor, and motion stages of the operation unit of FIG. 3.

FIG. 4 illustrates a thin specimen block slice 301 that has been sectioned or microtomed from the top side of donor block 29, and placed on, for example, a glass slide 11. Such slices can be, for example, about 5 μm thick, and can be used to find an area of interest in specimen 29a. The slide-mounted slice 301 and donor block 29 can be placed on stage 21, and can be held in registration by registration surfaces 21a of stage 21. Slice 301 and block 29 optionally have respective fiducial holes which can be aligned, and/or registration between the specimen slice 301 and specimen 29a of block 29 may be provided by affixing the exposed surface of specimen 29a to slide 11 while aligning edges of slide 11 with cassette 29c prior to cutting slide 301 from block 29. A variety of alternating slide/block registration techniques could also be used. Regardless, it is possible to examine slice 301 for an area of interest, and to determine the corresponding location on specimen 29a of donor block 29. Specimen 29a of donor block 29 can be sampled from these areas of interest using punch tube array 28 for further evaluation in a sample microarray.

FIG. 3 shows slide-mounted slice 11 and donor block 29 situated on stage 21 of control unit 10. Under suitable magnification, a cross-hair in an eyepiece can be placed in the center of a fiducial hole of the slice. Block 29 can be positioned so that the corresponding fiduciary hole of block 29 is in appropriate alignment through the use of the laser alignment system described above, as laser beam 53 should be aligned with the corresponding block fiducial hole. When a first set of corresponding fiduciary holes are aligned, a second set of holes can then be aligned to effectively coordinate the orientation of slide-mounted slice 11 and block 29. Optionally, photodetectors may be placed above and/or below block 29, so that the block can be aligned by moving the block until the laser light 53 falls directly on a lower photodetector, and no laser light is reflected back to an off-axis upper photodetector, or the like.

A variety of approaches may be used to prepare sample receptacle or punch tube arrays. According to one embodiment of the present invention, receptacles of the array can be shaped as a round tube, thus providing a circular sample cross section. In other embodiments, the cross section of the receptacle can take a variety of shapes including triangular, rectangular, and the like.

As described above with reference to FIG. 5, distal ends of the punch tubes can be plunged into a donor block that contains a tissue specimen, and each punch tube can capture a sample 75. FIG. 5 shows a receptacle array 28 containing a plurality of individual receptacles 28a. Array 28 can be coupled with platform 36. By advancing each punch tube distally into specimen 28a, each punch tube can capture an associate sample. Hence, it is possible to prepare a sample array from a single specimen. It is also possible to capture an array of samples from a plurality of donor blocks 29, or to capture an array of samples from a donor block 29 containing a plurality of biological specimens 29a.

Punch tubes 28a, 28b, . . . often also capture portions of paraffin or other embedding agents from the donor block 29, as well as samples. In the setup shown in FIG. 5, the samples 75 are located toward the top of donor block 29. After each punch tube engages the donor block 29, samples 75 can be disposed toward the proximal end of the punch tube receptacles, and paraffin or embedding agents can be disposed distal to sample portion of core samples 75, as shown in FIG. 5. By positioning the specimen 29a along a top surface of block 29, the embedding agent may instead be distal of the sample 29a in the punch tubes. As noted above, donor specimen block 29 can be prepared with a cassette having a central opening to facilitate cutting of microarray slides from the top or bottom of the block.

Figure 8:
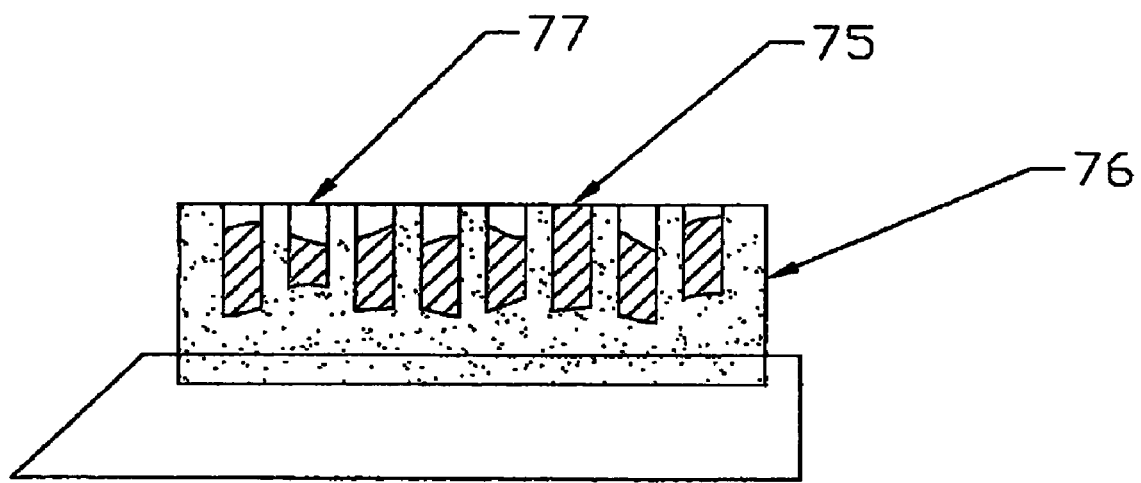
FIG. 8 illustrates one example of a tissue block arrangement.

During preparation of a sample array the tissue samples 75 that are contained in the punch tubes of punch tube array 28 may be of random lengths and heights due to the various thicknesses of the specimen and paraffin in the tissue block 29. FIG. 8 illustrates one approach to preparing a sample microarray block 76, wherein the samples or tissue columns from punch tube array 28 are embedded or extruded directly into an embedding agent such as a paraffin block. Such a procedure can result in sample microarray block 76 having tissue columns wherein the tissue sample portions of individual samples 75 are not horizontally aligned. When the sample microarray block 76 is microtomed, the result can be that some elements in a resulting sample microarray block slice are void of tissue or sample.

Figure 9:
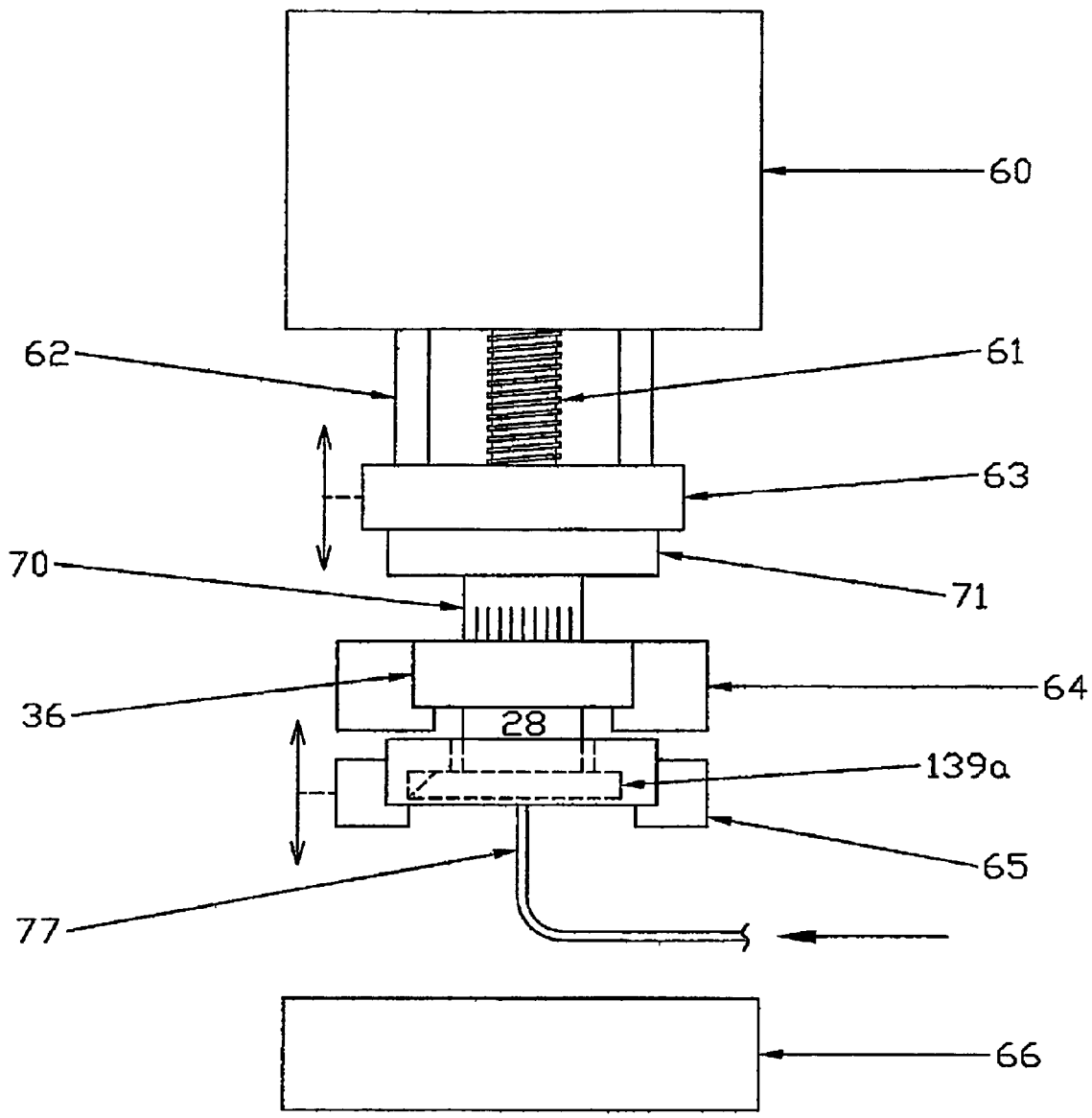
FIG. 9 is a side view schematically illustrating an embedding station according to one embodiment of the present invention.
Figure 11:
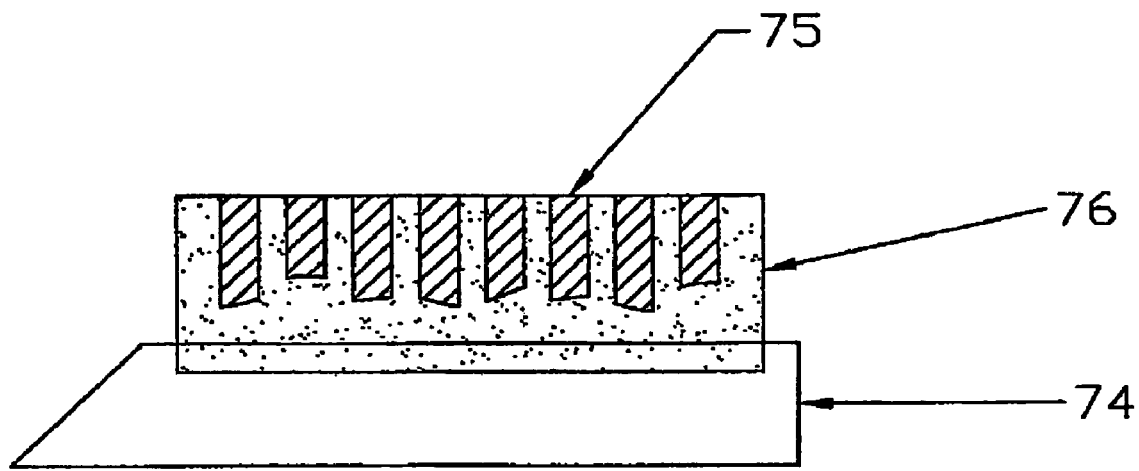
FIG. 11 illustrates a completed microarray column tissue block according to one embodiment of the present invention.

One embodiment of the present invention provides an embedding process that results in each tissue column having a sample surface that is flush with the top of the block 76, as shown in FIG. 11. According to the embodiment illustrated in FIG. 9, a compact embedding fixture is erected on a base plate 66. Handheld switch 30 can enable the operator to activate a variable speed motor drive that is in operative association with plunger array platform 71. The motor drive 132 can be contained in a motor housing 60a, and can be arranged to drive a lead screw 60b that is coupled with an upper jaw vise 63. Movement of upper jaw vise 63 in the vertical direction (as indicated by the arrow) can be guided by one or more vise rods 62. CTA platform 36 can be aligned with an array of plunger rods 70 and placed on a stationary stage 64. One or more loaded punch tubes 28a of array 28 can be extended into a mold 139a that can be adjusted vertically. When switch 30 is activated, mold stage 65 can move at the same speed as upper jaw vise 63. As a result of upward movement of the array 28 and mold 139a, the plungers of plunger array 70 extend into the punch tubes and extrude the samples therefrom. Furthermore, mold 139a can be temperature controlled so that heat can be added to and extracted from it. A flow tube 77 can inject a controllable amount of heated paraffin liquid or other embedding agent into mold 139a.

Figure 10:
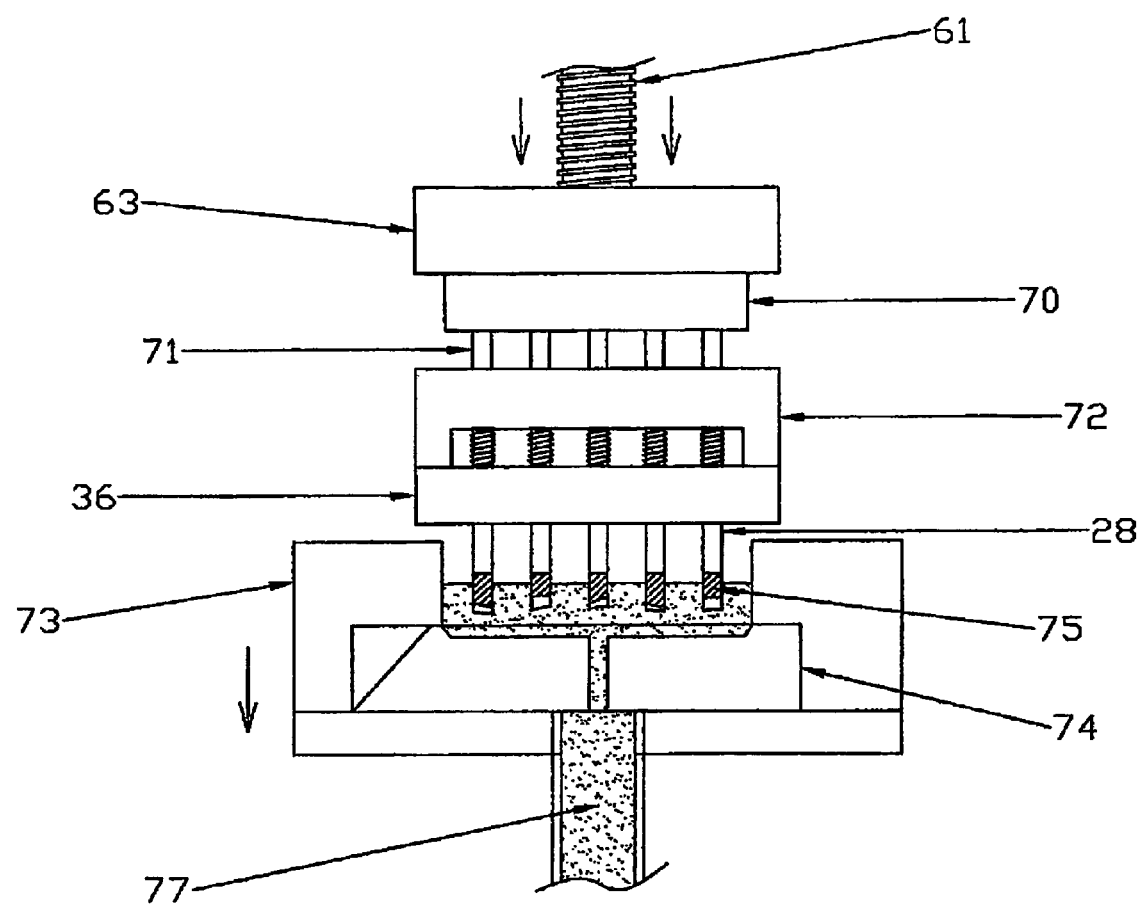
FIG. 10 is a side view schematically illustrating a method of embedding using an embedding station similar to that of FIG. 9.

FIG. 10 provides an illustration of the plunger system 130, according to one embodiment of the present invention. In this embodiment, CTA platform 36 and punch tube array 28 can be coupled with stationary stage 72 so that the punch tubes are extended distally. Plunger array 70 typically includes individual plungers of equal length so that distal surfaces of the plungers (and proximal surfaces of the samples 75) are aligned. Plunger array 70 can be coupled with plunger array platform 71. One or more individual plungers of plunger array 70 can be brought into contact with, and inserted into, one or more individual punch tubes of array 28 that is coupled with CTA platform 36. Mold 139a and a cassette platform 74 can be on mold stage 73. Mold stage 73 can be raised initially so that the distal ends of punch tubes of array 28 are near to the bottom of mold 139a. Mold 139a can be initially heated to above the melting temperature of the paraffin or other embedding agent. Flow tube 77 can be attached to the bottom of mold 139a.

As upper jaw vise 63 engages plunger array platform 71, one or more of the tissue columns or samples 75 can be simultaneously extruded from the punch tubes of array 28. The motion of upper jaw vise 63 can be mechanically linked to or otherwise coupled with mold stage 73 so that both upper jaw vise 63 and mold 139a move at the same speed. Accordingly, the extruded tissue columns or samples 75 may remain stationary with respect to mold 139a while punch tubes 28 are receding proximally from mold 139a. As shown in FIG. 10, warm paraffin liquid or other embedding agent can flow through flow tube 77 and into mold 139a from the bottom. The flow of embedding agent into mold 139a can be interrupted when tissue columns or samples 75 have been extruded to the point that the proximal end portions (e.g. 2 mm) of the tissue columns are still attached with the distal ends of the punch tubes. This can prevents the tissue columns from falling into the paraffin liquid or embedding agent. Mold 139a can then be cooled or allowed to cool to solidify the paraffin or embedding agent, thus resulting in a sample microarray block 76. The final proximal ends of the tissue samples 75 can then be completely expelled from punch tube arrays 28. As the samples 75 are thereby fixed in their respective positions in sample microarray block 76, more liquid paraffin or embedding agent can be flowed into the top of mold 139a to cover the top proximal ends of the tissue columns.

FIG. 11 shows a cross section of a completed sample microarray block 76 according to one embodiment of the present invention. In this embodiment, the proximal ends of all tissue columns 75 are aligned flush to the topside of sample microarray block 76. In this way, block 76 can be microtomed such that no element of the array on the specimen slide will be void of tissue.

It may be desirable to extrude all sample portions 75 simultaneously. Optionally, it may be desirable to extrude sample portions 75 sequentially. Such manipulation of the extrusion process can be effected by similar motion control mechanisms.

In some embodiments, the sample capture and sample extrusion procedures will occur on the same operation unit. In other embodiments, one operation unit 10 can be used for sample capture procedures, and another operation unit can be used for sample extrusion procedures. The components of operation unit 10 can be detachable, for example, a sample receptacle array 28 can be loaded with one operation unit, and then detached with platform 36 and coupled to another operation unit 10 for the extrusion process. A cassette can be placed on top of the microarray block to prepare the block for sectioning to microarray sections and/or slides.

In some embodiments, the mold 139a may be lined with tape, or any other suitable adhesive substance, such that samples 75 can be in adhesive connection with the mold. In one method of the present invention, the approximately 2 mm of sample 75 can be extruded from the punch tube onto mold 139a, and a first amount of embedding agent is added to mold 139a to a depth of about 2 mm and allowed to cure. The balance of the sample portion can then be fully extruded from the receptacles, and a second amount of embedding agent can be added to the mold 139a and allowed to cure, thus forming the sample microarray block 76. Optionally, the initial embedding or curing agent may comprise paraffin with a different melting and/or curing temperature than the subsequent embedding agent portion. For example, a higher melting/curing temperature paraffin may be used to initially form the tissue block. A lower melting/curing temperature paraffin can then embed the column tissue samples. This may inhibit deformation of the embedding tissue columns which might otherwise occur due to temperatures of the embedding agent. A cassette can be placed on top of the mold to prepare the mold for sectioning. Alternatively, the contents of sample array 28 can be directly extruded into a pre-formed recipient block, to form a sample microarray block 76.

Once formed, the tissue microarray block can be sectioned. This process typically involves cutting the block transverse to the longitudinal axis of the core samples. Slices can then be mounted on glass slides for further evaluation, including histochemical, immuno-histochemical, or molecular analysis and the like. Optionally, the sample microarray block may be stored for analysis at a later time.

Figure 12:
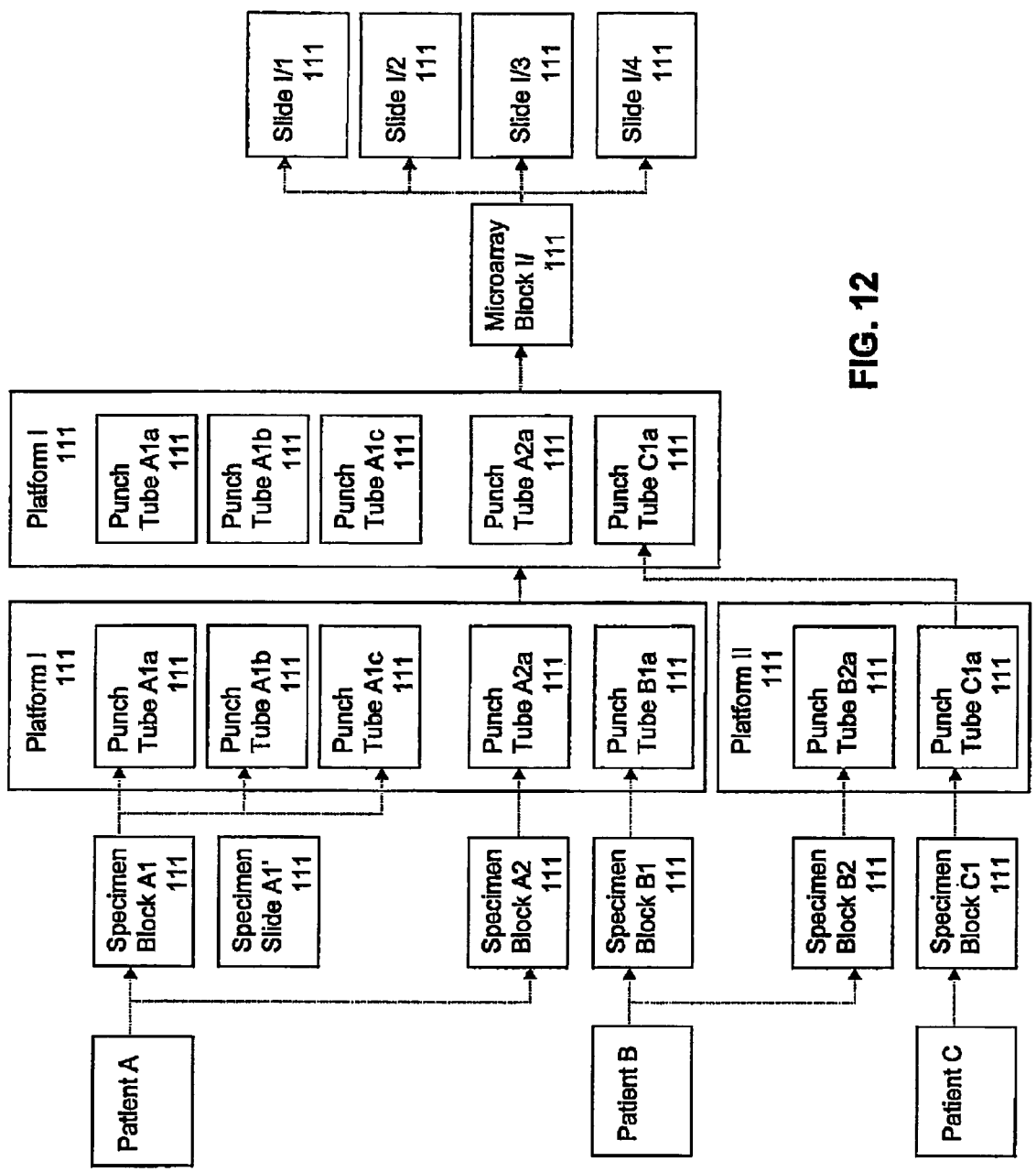
FIG. 12 is a block diagram schematically illustrating relationships between patients, microarray tissue slide test tissues, and intermediary tissue configurations and associated structures of the workstation of FIG. 1.

Referring now to FIG. 12, the systems, devices, and methods described herein are particularly well suited for handling large numbers of tissues from a large number of patients and for correlating tissue analysis performed within microarray slides or the like with the appropriate tissue source. For example, as schematically illustrated in FIG. 12, multiple patients A, B, C . . . each provide at least one tissue specimen from which an associated specimen block is formed. Specimen block A1 and specimen block A2 are both prepared from tissue specimens taken from patient A, while specimen block B1 is taken from patient B, and the like. In the exemplary method and system, a label 111 is attached to each specimen block. The labels will each preferably comprise a machine readable structure such as a radiofrequency identification tag, a bar code, or the like, and each label will typically indicate an identifier which is unique and/or otherwise differentiable from other identifiers of other structures of the system. A specimen slide A1' is sectioned from specimen block A1 as described above regarding specimen section 301 being taken from specimen block 29. This allows the specimen slide to be used for visually directing removal of selected sample tissues from sample locations of the specimen block by moving stage 21 while maintaining registration between the specimen slide and specimen block thereon. As tissues will often be removed solely from the block while the operation is directed with reference to the specimen slide, it may be advantageous to display a marker on an image of the specimen slide indicating the associated candidate sample location. As the specimen stage 21 will often move relative to a field of view of an image capture device (such as an objective lens of microscope 22 or a CCD camera 23) while the image capture device remains fixed, providing the candidate sample marker location may be provided by superimposing a reticle or other graphical marker at a fixed location on display 601 or through binocular eye piece 25.

Attaching labels 111 to the specimen blocks may be performed when the specimen blocks are made from the tissue specimens, such as by molding the marker into the specimen block, including the marker on the cassette structure, or the like. The specimen block should be labeled in a manner that helps assure that the specimen block identifier is properly associated with the correct patient, and often the correct tissue location from which the specimen was removed from that patient.

As described above, an array of punch tubes are supported by a platform indicated in FIG. 12 as platform I supporting punch tubes A1a, A1b . . . . Here, platform I also includes punch tubes which are used to take samples from specimen block A2 (also from patient A), as well as from specimen block B1 (having a tissue specimen taken from patient B). Each punch tube has a label with an associated identifier, and the punch tubes are removably and replaceably mounted to platform I. As each tissue sample is taken from its associated specimen block, the system may record both the association between the punch tube and a specimen block. This can be done, for example, by having the operation unit read the RFID tag of a punch tube in the specimen block RFID tag each time a punching operation is performed. The identifiers associated with the specimen block and punch tube can be recorded, and the location from which the sample taken by the punch tube can also be recorded. Sample locations may comprise x-y coordinates as read from the specimen stage 21, or the like. Alternatively, the specimen location may be recorded as a graphical data file with an image of the specimen slide having the sample location marker superimposed thereon.

After at least a portion of the punch tube array of platform I contained associated samples, it may be desirable to remove at least some of the punch tubes from the platform and/or add new punch tubes to the platform. As the platform and/or each individual punch tube is labeled, and as the tissue samples are contained within the receptacles of the punch tubes, the platform assembly and/or individual punch tubes may be stored or archived. Regardless, once platform 1 has the tissue samples and associated punch tubes that are desired to be included in a microarray block Ii, the samples can be extruded either sequentially or simultaneously as described above. Once again, microarray block Ii will typically be labeled, and the label may be incorporated as the block is formed by including an RFID device or other label in the mold, using a label which is attached to the cassette or the like. Associations between the microarray block Ii and the tissue samples of platform 1 at the time the microarray block is formed can be recorded at the time the samples are extruded. Hence, such associations may be recorded automatically by operation unit 10. In some embodiments, the operation unit will prompt the system operator to record the associations between these intermediary tissue configurations.

Microarray block Ii is sectioned into a plurality of microarray slides Ii1, Ii2 . . . as described above. Once again, each microarray slide may be labeled with a label 111. These labels may be included on the slide glass, maybe taped onto the slide glass, or the like. Advantageously, each microarray tissue element of each slide can be associated with a particular patient, and with each intermediary tissue configuration. The location of the sample tissue of the tissue specimen may also be documented. Including samples from other patients in the microarray block, such as by removing and replacing a punch tube with a sample taken from specimen block C1 from patient C as illustrated in FIG. 12 does not lead to an error in the biological test results, as the system associates each tissue element of the microarray with the appropriate patient.

A simplified data structure showing the associations between the patient identifiers, specimen block identities taken from specific patients, punch tube identifiers of punch tubes containing samples taken from specific specimens and the like are illustrated. Note that a large number of punch tubes may be included in a single platform, and that the punch tubes in the associated tissue samples may be removed from the platform and replaced by an alternative tissue sample as described above regarding FIG. 12.

Figure 13:
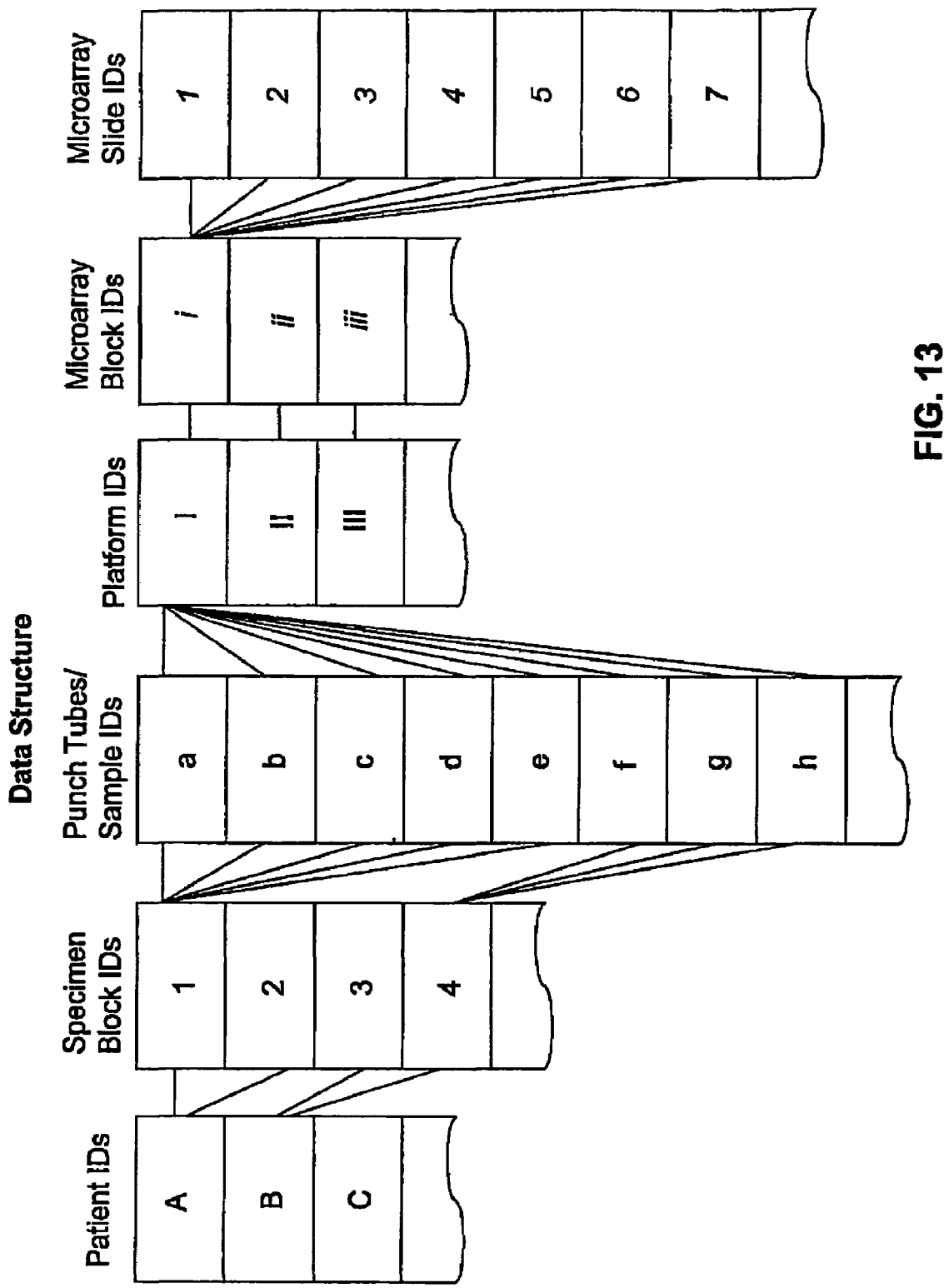
FIG. 13 is a block diagram schematically illustrating a data structure for identifying patients, microarray tissue slide test tissues, and intermediary tissue configurations and associated structures of the workstation of FIG. 1.

In the data structure illustrated in FIG. 13, the platform identifiers are each associated with a single microarray block identifier, as all punch tubes of a platform are extruded into a single microarray block. Alternative arrangements may selectively extrude a subset of the punch tubes from the platform, the platform may be used only for tissue sample removal from specimens with the punch tubes used individually during extrusion, or the like. Regardless, the microarray slide identifiers are preferably associated with the microarray block identifier from which they are sectioned.

As described above, the identifiers can, but need not be limited to information stored on the label. For example, the label may provide sufficient data to identify a specific punch tube, and the punch tube associations (optionally including associated specimen blocks, platform identifications, microarray slides, patients, sample locations, and the like) can then be accessed. In either case, the data structure can provide a continuous documented chain between a specific patient and a particular tissue sample location within a microarray slide, as well as optionally providing information regarding the specimen location, and the like.

It will be understood that the procedures and methods described herein can be carried out under a variety of carefully controlled conditions. For example, the workstation and/or embedding station can be maintained at or below the freezing point of a particular sample specimen, or in a refrigerated environment. Certain components of the stations, for example the platforms, can be made of high thermal conductivity material such as copper. Relatedly, certain components, for example the receptacles, may be made of beryllium copper, which can be heat hardened. Cooling of the components can be accomplished by a Peltier effect device. Temperature sensing can be accomplished by using a thermal couple attached to certain components of the stations, for example the array platform.

Although the methods, devices, and systems of the present invention are described primarily in the context of tissue microarrays, it should be understood that the techniques of the present invention may be adapted for use in preparing microarrays of any of a variety of biological samples, including cell samples, fluid samples, and the like.

What is claimed is:

1. A method for preparing a microarray from a tissue specimen, the method comprising:

extending a plurality of punch tubes from a punch tube platform so that a distal end of each punch tube advances sequentially into the tissue specimen and an associated tissue sample protrudes into a sample receptacle of the punch tube, wherein the platform holds at least 5 punch tubes in a two dimensional punch tube array so that the punch tubes slide along parallel longitudinal axes;

removing the punch tubes and the associated tissue samples from the tissue specimen, wherein the sample receptacle of each punch tube punches the associated sample with a sample cross-section in a tissue microarray sample size range, and wherein the platform supports each punch tube with a separation from adjacent punch tubes in a tissue microarray sample separation range; and simultaneously extruding at least some tissue samples into an extrusion receptacle while the punch tubes are supported by the platform.

2. The method of claim 1, wherein a plurality of other platforms each have openings for receiving punch tubes, and further comprising recording a platform identifier associated with each platform.

3. The method of claim 2, wherein each platform has a platform label indicating the associated platform identifier, the platform label comprising at least one member selected from the group consisting of a bar code and an RFID (Radio Frequency Identification) device.

4. The method of claim 1, further comprising cryogenically cooling at least one of the tissue specimen, the punch tubes, and the platform.

5. The method of claim 1, wherein the at least some tissue samples are extruded by a plunger array having a plurality of plungers, the plungers of the plunger array corresponding to the at least some punch tubes as supported by the platform and having aligned distal plunger surfaces so that the at least some extruded samples have aligned proximal surfaces.

6. The method of claim 5, wherein the at least some sample portions are extruded toward a mold, and further comprising adding an embedding agent to the mold and allowing the embedding agent to cure so as to form a tissue sample microarray block.

7. The method of claim 6, wherein a plurality of other tissue sample microarray blocks are formed with other tissue samples, and further comprising recording a microarray block identifier associated with each microarray block.

8. The method of claim 7, wherein each microarray block has a microarray block label indicating the associated microarray block identifier, the microarray block label comprising at least one member selected from the group consisting of a bar code and an RFID (Radio Frequency Identification) device.

9. The method of claim 6, further comprising separating a plurality of microarray sections from the microarray block.

10. The method of claim 9, further comprising recording a microarray section identifier associated with each microarray section.

11. The method of claim 10, further comprising labeling each microarray section with a microarray section label indicating the associated microarray section identifier, the microarray section label comprising at least one member selected from the group consisting of a bar code and an RFID (Radio Frequency Identification) device, and further recording an association between the microarray section identifier and the tissue samples, the tissue specimen, and an associated patient.

12. The method of claim 11, further comprising cryogenically cooling at least one of the tissue samples, the tissue specimen, and the platform.

13. The method of claim 1, further comprising recording an identifier associated with each punch tube, each punch tube identifier associated with a tissue specimen identifier and a patient identifier.

14. The method of claim 13, wherein the each punch tube has a punch tube label indicating the punch tube identifier, the punch tube label comprising at least one member selected from the group consisting of a bar code and an RFID (Radio Frequency Identification) device.

15. The method of claim 1, further comprising at least one of:
a) removing at least some of the punch tubes from the platform while the removed punch tubes contain the associated tissue samples, mounting at least one of the removed punch tubes on another platform, the other platform receiving a second plurality of punch tubes including the at least one punch tube, the second plurality of punch tubes each having an associated tissue sample; and
b) archiving at least one of the tissue samples within the associated punch tube for use significantly after removal of the at least one tissue sample from the tissue specimen.

16. The method of claim 1, wherein the punch tubes are extended distally into the tissue specimen by an arbor.

17. The method of claim 16, further comprising urging each punch tube proximally from the tissue specimen using a spring, the arbor resiliently deforming the spring during extension.

18. The method of claim 16, wherein the arbor simultaneously advances at least two of the punch tubes into the tissue specimen.

19. The method of claim 16, wherein the arbor sequentially advances a second punch tube after a first punch tube, and further comprising repositioning the tissue specimen relative to the arbor by transmitting drive signals to a first motion stage after the first punch tube captures a first associated tissue sample from a first location of the tissue specimen.

20. The method of claim 19, further comprising manually inputting the second location to an input device with reference to a slide tissue corresponding to and separated from the tissue specimen, wherein the first stage moves the slide tissue and the tissue specimen while maintaining registration therebetween.

21. The method of claim 20, further comprising viewing a display showing an image of the slide tissue and a target marker identifying a candidate location for a subsequent tissue sample thereon, wherein the first motion stage effects lateral movement of the target marker to an alternative candidate location by moving the slide tissue laterally relative to a field of view of an image capture device coupled to the display, the arbor remaining aligned with the image capture device during movement of the first stage.

22. The method of claim 21, further comprising displaying, on the slide tissue image, a plurality of prior punch tube sample locations.

23. The method of claim 19, further comprising repositioning the platform relative to the arbor by transmitting drive signals to a second motion stage after the first punch tube captures the first tissue sample.

24. The method of claim 23, further comprising zeroing the first and second stages by transmitting light from an illumination source to at least one light sensor, the illumination source at a fixed reference location during motion of the first and second motion stages, wherein a first registration aperture adjacent a platform receptacle is used for zeroing the second motion stage, and wherein a second registration aperture adjacent a specimen receptacle is used for zeroing the first motion stage, the zeroing comprising maximizing the light through the apertures.

\* \* \* \* \*